United States Patent [19]

Ohura et al.

[11] 4,238,411

[45] Dec. 9, 1980

[54] METHOD OF RECOVERING THIOUREA DIOXIDE

[75] Inventors: Osami Ohura; Osamu Fujimoto, both of Fuji, Japan

[73] Assignee: Tokai Denka Kogyo Kabushiki Kaisha, Ohtemachi, Japan

[21] Appl. No.: 55,787

[22] Filed: Jul. 9, 1979

[30] Foreign Application Priority Data

Jul. 25, 1978 [JP] Japan .................................. 53/89985

[51] Int. Cl.$^3$ .......................................... C07C 145/00
[52] U.S. Cl. .................................................. 260/513.7
[58] Field of Search ...................................... 260/513.7

[56] References Cited

U.S. PATENT DOCUMENTS

| | | | |
|---|---|---|---|
| 2,150,921 | 3/1939 | Havas | 260/513.7 |
| 2,347,446 | 4/1944 | Walker | 260/513.7 |
| 2,783,272 | 2/1957 | Young | 260/513.7 |

FOREIGN PATENT DOCUMENTS

| | | | |
|---|---|---|---|
| 45-17665 | 6/1970 | Japan | 260/513.7 |
| 50-62934 | 5/1975 | Japan | 260/513.7 |

*Primary Examiner*—Nicky Chan
*Attorney, Agent, or Firm*—Scully, Scott, Murphy & Presser

[57] ABSTRACT

According to this invention there is provided a method of recovering thiourea dioxide characterized in that in the production of thiourea dioxide by the reaction of thiourea and hydrogen peroxide in an aqueous solvent, the waste liquor after separation of the crystals of thiourea dioxide after reaction is treated with an ion-exchange resin to remove side reaction products and impurities contained therein, and is then concentrated with a reverse-osmotic membrane to crystallize the thiourea dioxide dissolved therein.

13 Claims, No Drawings

METHOD OF RECOVERING THIOUREA DIOXIDE

BACKGROUND OF THE INVENTION

1. Field of the Invention

This invention relates to the method of recovering T.U.D. dissolved in the waste liquor which is produced in the production of thiourea dioxide (hereinafter referred to as "T.U.D.").

2. Description of the Prior Art

Among the methods of production of T.U.D. there have been announced various reports on the method of its production by reaction of thiourea and hydrogen peroxide in a solvent.

The solvents used in such reported methods are broadly classified into non-aqueous and aqueous solvents.

The production of T.U.D. by the reaction of thiourea and hydrogen peroxide in a non-aqueous solvent (chlorinated solvents such as crbon tetrachloride and chloroform as well as lower aliphatic alcohols) has been proposed by German Pat. No. 917553, Italian Pat. No. 579119 and French Pat. No. 2040797. This proposed method is advantageous in that T.U.D. as the reaction product can all be recovered as cryatals because it does not dissolve in the solvent. But such method is disadvantageous in that since the reaction of thiourea and hydrogen peroxide is a heterogeneous reaction, there are produced by-products in large quantities and these by-products do not dissolve in the solvent, so they are incorporated into the product T.U.D., thus causing the purity of the product to deteriorate, and besides the solvent used is lost in large quantities. Thus, an industrial adoption of such method involves many disadvantages.

On the other hand, in the case of production of T.U.D. in an aqueous solvent, the starting thiourea dissolves well in water and forms homogeneous phase. Since the reaction of thiourea and hydrogen peroxide is very fast, their reaction in a homogeneous phase is advantageous in that the formation of by-products is less in quantity and T.U.D. can be obtained in high yield and high purity.

However, the said method is disadvantageous in that the quantity of T.U.D. crystals obtained becomes smaller because part of the reaction product T.U.D. is dissolved in the waste liquor after separation of the T.U.D. crystals formed.

To eliminate this drawback, U.S. Pat. No. 2,783,272 and Japanese patent publication No. 17665/1970 propose a method in which such waste liquor is re-used as a reaction solvent to recover T.U.D. dissolved therein. According to such method, however, a repeated re-use of the waste liquor causes a correspondingly increasing accumulation in the reaction solution by-products, e.g. sulfuric acid, as well as impurities contained in the starting thiourea and hydrogen peroxide, resulting in that the yield and purity of T.U.D. lower.

Japanese patent publication No. 17765/1970 proposes a method in which the waste liquor is treated with a carbonate or hydroxide of an alkaline earth metal, which is a metal of Group IIa of the Periodic Table, to neutralize the sulfuric acid contained therein, and after separation of the resulting precipitate of a sulfate the waste liquor is re-used as a reaction solvent.

Treating the waste liquor in such a manner somewhat improves the yield and purity of T.U.D. as compared with the case where the said treatment is not applied, but does not afford a satisfactory result.

Although the above treating method can remove sulfuric acid contained in the waste liquor, it cannot remove other side reaction products and impurities derived from the starting thiourea and hydrogen peroxide, so that also in this treating method impurities accumulate in the reaction solution as the re-use of the treated waste liquor is repeated, which impurities not only hinder the reaction of thiourea and hydrogen peroxide but also contaminate the reaction product T.U.D., and thus a satisfactory result is not obtained. According to the Japanese patent publication referred to above which proposes this treating method, the neutralizer used therein does not promote the decomposition of T.U.D. However, in case such neutralizer is added in excess by mistake, there occurs a vigorous decomposition of T.U.D.; therefore, even if the waste liquor after neutralization is re-used to prepare T.U.D., there can be expected no improvement in the yield of T.U.D.

Furthermore, the neutralizer used in the waste liquor treatment is dissolved in the treated waste liquor, so the re-use of the latter causes lowering of the purity of the resulting T.U.D. This drawback is pointed out in Japanese patent public disclosure No. 62934/1975.

From a common-sense point of view, the evaporation method is considered as the method of recovering T.U.D. contained in the waste liquor, but an industrial adoption thereof has been impossible because of the following drawbacks: at the time of concentration T.U.D. undergoes a thermal decomposition resulting in decrease of its quantity recovered, and since the by-products dissolved in the waste liquor as well as the impurities derived from the starting thiourea and hydrogen peroxide are recovered at the same time, the purity of the recovered T.U.D. lowers.

SUMMARY OF THE INVENTION

Having made a keen study about the method of recovering T.U.D. in high yield and high purity which is dissolved in the reaction waste liquor resulting from the reaction of thiourea and hydrogen peroxide in an aqueous solvent, we invented a method of recovering T.U.D. of high purity in high yield in which, as set forth hereinbefore, the waste liquor is treated with an ion-exchange resin and the impurities therein removed, and is then concentrated with a reverse-osmotic membrane.

DESCRIPTION OF THE INVENTION

The treating process using an ion-exchange resin aims at removing impurities contained in the waste liquor, namely impurities derived from the starting thiourea and hydrogen peroxide, as well as reaction by-products, e.g. sulfuric acid, in order to improve the purity of T.U.D. obtained by the concentration of the waste liquor with a reverse-osmotic membrane. But it also has advantages based on such treatment. Most reverse-osmotic membranes except some special ones are poor in acid resistance, so in case waste liquor is concentrated without treatment with an ion-exchange resin it is necessary to choose a special expensive membrane. On the other hand, reaction waste liquors once treated with an ion-exchange resin allow the use of a generally-used cheap membrane.

Another advantage is that since impurities and by-products are removed by the treatment with an ion-exchange resin, the concentration of the substances dissolved in the waste liquor becomes lower, so that the concentration rate for the waste liquor with a reverse-osmotic membrane can be improved.

Regarding the ion-exchange resins used in the present invention, even with an anion exchange resin alone there can be attained a little improvement over the method disclosed in the Japanese patent publication 17665/1970, but if it is used together with a cation exchange resin, the waste liquor treatment becomes more effective.

Anion exchange resin are used for the purpose of removing sulfate ion formed by the reaction of thiourea and hydrogen peroxide, phosphate ion incorporated from hydrogen peroxide, and chloride ion derived from thiourea. Anion exchange resins of any kind may be used in the present invention.

The use of cation exchange resin aims at removing heavy metal ion, alkali metal ion and alkaline earth metal ion derived from the starting thiourea and hydrogen peroxide, as well as by-products having a cation valency produced by the reaction of thiourea and hydrogen peroxide. But the by-products of unknown structure resulting from the reaction of thiourea and hydrogen peroxide are weakly basic substances, so the use of strongly acidic cation exchange resins is desirable to improve their removal.

Regarding the treating method, an ion-exchange resin may be added into the waste liquor, but passing the waste liquor through a column charged with an ion-exchange resin is more simple and convenient industrially.

The waste liquor treated with an ion-exchange resin is, as it is, treated with a reverse-osmotic membrane.

Employable as the membrane material are acetylcellulose, aromatic polyamide, benzimidazoline, and polysulfone. These membranes may take any of flat, spiral, tubular, and hollow fiber shapes.

The operation pressure ranges from 3 to 100 $kg/cm^2$ and preferably from 30 to 80 $kg/cm^2$.

Regarding the concentration rate for waste liquor, if it is too low, the recovery of T.U.D. becomes low, while if it is too high, it becomes necessary to increase the operation pressure, which causes a problem in point of the pressure resistance of membrane, so its value ranges from 2 to 10 times and preferably from 3 to 6 times in terms of concentration of the waste liquor.

The treatment temperature in the treating method of the present invention is not higher than 15° C. and preferably not higher than 10° C. in order to minimize the decomposition of T.U.D. during the treating process and also to minimize the dissolution of T.U.D. in the waste liquor to be treated.

The treating method of the present invention can be applied to all waste liquors obtained in the production of T.U.D. by the reaction of thiourea and hydrogen peroxide is an aqueous solvent no matter what the reaction condition and reaction system may be.

However, if hydrogen peroxide remains in the waste liquor obtained, a long period of use can cause deterioration of ion-exchange resin and reverse-osmotic membrane, so in such a case it is necessary to decompose the residual hydrogen peroxide in advance with a reducing agent such as sulfurous acid or sulfite, and then treat the waste liquor.

The waste liquor after separation of T.U.D. through concentration with a reverse-osmotic membrane is mixed with a waste liquor which also is to be treated according to the method of the present invention, whereby most of the T.U.D. dissolved therein can be recovered.

DESCRIPTION OF PREFERRED EMBODIMENTS

A working example of the present invention is given below, but this is for illustration only and is not intended to restrict the invention.

Example 25 g of thiourea was dissolved in 250 ml of pure water and the solution cooled to 8°–10°C., at which temperature was added 49 g of a 50% aqueous hydrogen peroxide solution over a period of 90 minutes while the reaction solution was stirred. Then, after ageing at 8°–10° C. for 30 minutes with continued stirring of the reaction solution, the resulting T.U.D. crystals were separated. The yield of T.U.D. thus obtained as well as the waste liquor quantity and its composition are as follows:

Yield of T.U.D. crystals—24.9 g
Yield of T.U.D. (vs. thiourea)—70.17
Waste liquor quantity—280 ml
Waste liquor pH—1.8
T.U.D.—23.5 g/l (6.58 g)
$H_2SO_4$—7.4 g/l (2.07 g)

The waste liquor obtained by the above reaction was passed through a column charged with 25 ml of an anion exchange resin (Amberlite IRA-400) and 25 ml of a cation exchange resin (Amberlite IR-120B) while the waste liquor temperature was maintained at 8°–10° C., to obtain 245 ml of the treated solution, which was of the followng composition:

pH—6.0
T.U.D.—24.3 g/l

Then, 200 ml of the treated solution was placed in a tester in which was fixed a reverse-osmotic membrane formed of acetylcellulose having an area of 45 $cm^2$. Nitrogen gas was then introduced to the pressure of 50 $kg/cm^2$ and the solution was concentrated to 40 ml over a period of 6 hours while it was cooled to 8°–10° C., to give 3.7 g of T.U.D. crystals (76% recovery). The concentrated solution after separation of the crystals had the following composition:

pH—5.7
T.U.D.—25.6 g/l

We claim:

1. A method of recovering thiourea dioxide characterized in that in the production of thiourea dioxide by the reaction of thiourea and hydrogen peroxide in an aqueous solvent, the waste liquor after separation of the crystals of thiourea dioxide after reaction is treated with both an anion exchange resin and a cation-exchange resin to remove side reaction products and impurities contained therein, and is then concentrated with a reverse-osmotic membrance to crystallize the thiourea dioxide dissolved therein.

2. A method according to claim 1, in which said cation exchange resin is a strongly acidic cation exchange resin.

3. A method according to claim 1, in which the waste liquor to be treated is passed through a column charged with the ion-exchange resins and is thereby treated.

4. A method according to claim 1, in which said process is carried out at a temperature not higher than 15° C.

5. A method according to claim 1, in which hydrogen peroxide remaining in the waste liquor is decomposed in advance with a reducing agent and then the treatment with the ion-exchange resins and the concentration with a reverse-osmotic membrane are carried out.

6. A method according to claim 1, in which the material of said reverse-osmotic membrane is selected from the group consisting of acetylcellulose, aromatic polyamide, benzimidazoline, and polysulfone membranes.

7. A method according to claim 1, in which the shape of said reverse-osmotic membrane is selected from the group consisting of flat, spiral, tubular, and hollow fiber.

8. A method according to claim 1, in which the concentration of the waste liquor with a reverse-osmotic membrance is carried out at a pressure ranging from 3 to 100 kg/cm$^2$.

9. A method according to claim 1, in which the concentration rate for the waste liquor is 2 to 10 times in terms of concentration of the waste liquor.

10. The process of claim 4, in which said temperature is not higher than 10° C.

11. The process of claim 5, in which said reducing agent is selected from the group consisting of sulfurous acid and sulfite.

12. The process of claim 8, in which said pressure ranges from 30 to 80 kg/cm$^2$.

13. The process of claim 9, in which the concentration rate is 3 to 6 times in terms of concentration of the waste liquor.

* * * * *